(12) United States Patent
Handa et al.

(10) Patent No.: US 11,944,402 B2
(45) Date of Patent: Apr. 2, 2024

(54) SYSTEM AND METHOD OF VERIFYING USER INTERFACE DEVICE FUNCTION

(71) Applicant: Verb Surgical Inc., Santa Clara, CA (US)

(72) Inventors: Karan Handa, San Mateo, CA (US); Denise Ann Miller, Scotts Valley, CA (US); Joan Savall, Palo Alto, CA (US); Mufaddal Jhaveri, Fremont, CA (US)

(73) Assignee: Verb Surgical Inc., Santa Clara, CA (US)

( * ) Notice: Subject to any disclaimer, the term of this patent is extended or adjusted under 35 U.S.C. 154(b) by 799 days.

(21) Appl. No.: 17/026,080

(22) Filed: Sep. 18, 2020

(65) Prior Publication Data

US 2022/0087762 A1 Mar. 24, 2022

(51) Int. Cl.
*A61B 34/00* (2016.01)
*A61B 17/00* (2006.01)
*A61B 34/20* (2016.01)
*A61B 90/60* (2016.01)

(52) U.S. Cl.
CPC .... *A61B 34/74* (2016.02); *A61B 2017/00973* (2013.01); *A61B 2034/2051* (2016.02); *A61B 2034/2055* (2016.02); *A61B 90/60* (2016.02)

(58) Field of Classification Search
CPC .. A61B 2017/00725; A61B 2034/2051; A61B 2090/0811; A61B 90/60; B25J 9/1674
See application file for complete search history.

(56) References Cited

U.S. PATENT DOCUMENTS

| 5,410,488 A | * | 4/1995 | Andersen, III | ........ | G01B 7/023 |
| | | | | | 702/158 |
| 2012/0235029 A1 | * | 9/2012 | Tam | ...................... | G01D 18/00 |
| | | | | | 250/353 |
| 2013/0153755 A1 | * | 6/2013 | Pikkujamsa | ......... | H03K 17/941 |
| | | | | | 250/221 |
| 2018/0078319 A1 | * | 3/2018 | Nobles | .................... | A61B 34/74 |
| 2020/0336222 A1 | * | 10/2020 | Rimini | ................ | H04W 52/367 |
| 2022/0087762 A1 | * | 3/2022 | Handa | .................... | A61B 90/06 |

* cited by examiner

*Primary Examiner* — Vincent H Tran
(74) *Attorney, Agent, or Firm* — Aikin & Gallant, LLP (57) ABSTRACT

Surgical robotic systems, and methods of verifying functionality of a user interface device of such systems, are described. During a surgical procedure, the user interface device controls motion of a surgical tool. Proximity sensors of the user interface device generate proximity measures throughout the surgical procedure. The proximity measures are used to detect whether the user interface device is dropped and to responsively halt motion of the surgical tool. To verify an accuracy of the proximity sensors that provide the drop detection, a test is performed when the user interface device is placed in a dock. The test compares the generated proximity measures to expected proximity data. When the proximity measures match the expected proximity data, the system determines that the proximity sensors are functioning accurately and verifies that the user interface device is functioning safely. Other embodiments are described and claimed.

20 Claims, 6 Drawing Sheets

SYSTEM AND METHOD OF VERIFYING USER INTERFACE DEVICE FUNCTION

BACKGROUND

Field

Embodiments related to robotic systems are disclosed. More particularly, embodiments related to surgical robotic systems having user interface devices are disclosed.

Background Information

Minimally-invasive surgery, MIS, such as laparoscopic surgery, uses techniques that are intended to reduce tissue damage during a surgical procedure. Laparoscopic procedures typically call for creating a number of small incisions in the patient, e.g., in the abdomen, through which several surgical tools such as an endoscope, a scalpel, a grasper, and a needle, are then inserted into the patient. A gas is injected into the abdomen which insufflates the abdomen thereby providing more space around the tips of the tools, making it easier for the surgeon to see (via the endoscope) and manipulate tissue at the surgical site. MIS can also be performed using a robotic system in which the surgical tools are operatively attached to the distal ends of robotic arms, and a control system actuates the arm and its attached tool so that the latter mimics the movements and tool specific commands of a user input device (UID) as the latter is being manipulated by a surgeon in their hand.

SUMMARY

User input devices used to generate control commands to cause motion of surgical robotic system components may include sensors to detect whether a surgeon is holding the user input device, e.g., for drop detection. Functionality of such sensors can be critical to the success of the procedure. For example, if the sensors stop working during a long surgery, the sensors may not sense that the surgeon has dropped the user input device, which could lead to inadvertent motion of the surgical robotic system components. Existing surgical robotic systems, however, lack a means of verifying that drop detection sensors are working properly at a beginning or over a course of the surgery. Accordingly, a system and method for self-testing user input devices to verify an accuracy of drop detection sensors can contribute to successful robotic surgery.

A surgical robotic system and a method of verifying functionality of a user interface device of the surgical robotic system, are provided. In an embodiment, the method of verifying functionality of the user interface device includes determining whether the user interface device is positioned in a dock of a user console of the surgical robotic system. In response to determining that the user interface device is in the dock, proximity data is received from several proximity sensors of the user interface device. The proximity data indicates the presence (or absence) of nearby objects, such as a sidewall of the dock. The proximity data is compared to expected proximity data corresponding to an orientation of the user interface device in the dock. For example, the expected proximity data can correspond to expected proximity readings of the proximity sensors in a presumed orientation of the user interface device (such as a properly-seated orientation of the user interface device) or the expected proximity data can correspond to the expected proximity readings in a tracked orientation (using a tracking sensor) of the user interface device. The comparison can result in a match between the actual and expected proximity data, or no match between the actual and expected proximity data. Based on the comparison, an accuracy of the proximity sensors can be determined. For example, a match between the data can verify that the proximity sensors are accurate and the user interface device is functional. By contrast, when the comparison indicates that the actual and expected proximity data does not match, an alert can be provided to cause re-testing or re-calibration of the proximity sensors prior to continued use of the user interface device.

In an embodiment, the dock can have a movable portion, such as extendable prongs, that can constrain the docked user interface device. For example, the movable portion can move to a first state that orients the user interface device in a particular orientation, e.g., in the properly-seated orientation. The user interface device function can be tested in the first state. The movable portion may then be moved to a second state, e.g., retracted away from the user interface device. In the second state, second proximity data can be collected and compared to second expected proximity data for the configuration of the user interface device and the dock in the second state. Accordingly, additional test data can be collected and analyzed for a single device orientation. The sets of test data can be used to confirm the accuracy of the proximity sensors and verify the function of the user interface device.

The above summary does not include an exhaustive list of all aspects of the present invention. It is contemplated that the invention includes all systems and methods that can be practiced from all suitable combinations of the various aspects summarized above, as well as those disclosed in the Detailed Description below and particularly pointed out in the claims filed with the application. Such combinations have particular advantages not specifically recited in the above summary.

BRIEF DESCRIPTION OF THE DRAWINGS

The embodiments of the invention are illustrated by way of example and not by way of limitation in the figures of the accompanying drawings in which like references indicate similar elements. It should be noted that references to "an" or "one" embodiment of the invention in this disclosure are not necessarily to the same embodiment, and they mean at least one. Also, in the interest of conciseness and reducing the total number of figures, a given figure may be used to illustrate the features of more than one embodiment of the invention, and not all elements in the figure may be required for a given embodiment.

DETAILED DESCRIPTION

Embodiments describe methods of verifying functionality of a user interface device. The user interface device can control spatial motion of a surgical tool of a surgical robotic system during a robotic surgery. The user interface device may, however, be used in other robotic systems, such as for manufacturing or military applications, to name only a few possible applications.

In various embodiments, description is made with reference to the figures. However, certain embodiments may be practiced without one or more of these specific details, or in combination with other known methods and configurations. In the following description, numerous specific details are set forth, such as specific configurations, dimensions, and processes, in order to provide a thorough understanding of the embodiments. In other instances, well-known processes and manufacturing techniques have not been described in particular detail in order to not unnecessarily obscure the description. Reference throughout this specification to "one embodiment," "an embodiment," or the like, means that a particular feature, structure, configuration, or characteristic described is included in at least one embodiment. Thus, the appearance of the phrase "one embodiment," "an embodiment," or the like, in various places throughout this specification are not necessarily referring to the same embodiment. Furthermore, the particular features, structures, configurations, or characteristics may be combined in any suitable manner in one or more embodiments.

The use of relative terms throughout the description may denote a relative position or direction. For example, "upward" may indicate a first direction away from a reference point, e.g., away from a proximity sensor. Similarly, "downward" may indicate a location in a second direction opposite to the first direction, e.g., toward the proximity sensor. Such terms are provided to establish relative frames of reference, however, and are not intended to limit the use or orientation of a surgical robotic system component to a specific configuration described in the various embodiments below.

In an aspect, a surgical robotic system performs a self-test of a user interface device when the user interface device is docked. The self-test includes receiving proximity data from proximity sensors, which may be used for drop detection, and comparing the proximity data to expected proximity data. The expected proximity data can be based on a predetermined orientation, such as when the user interface device is properly seated in a dock, or based on tracking data from a tracking sensor of the user interface device. When the proximity data matches the expected proximity data, the surgical robotic system can determine that the proximity sensors are functioning accurately. Therefore, functionality of the user interface device is verified and the user may continue to use the user interface device. When the proximity data does not match the expected proximity data, however, an alert may be generated to initiate a re-check or a re-calibration of the user interface device prior to continued use.

Figure 1:
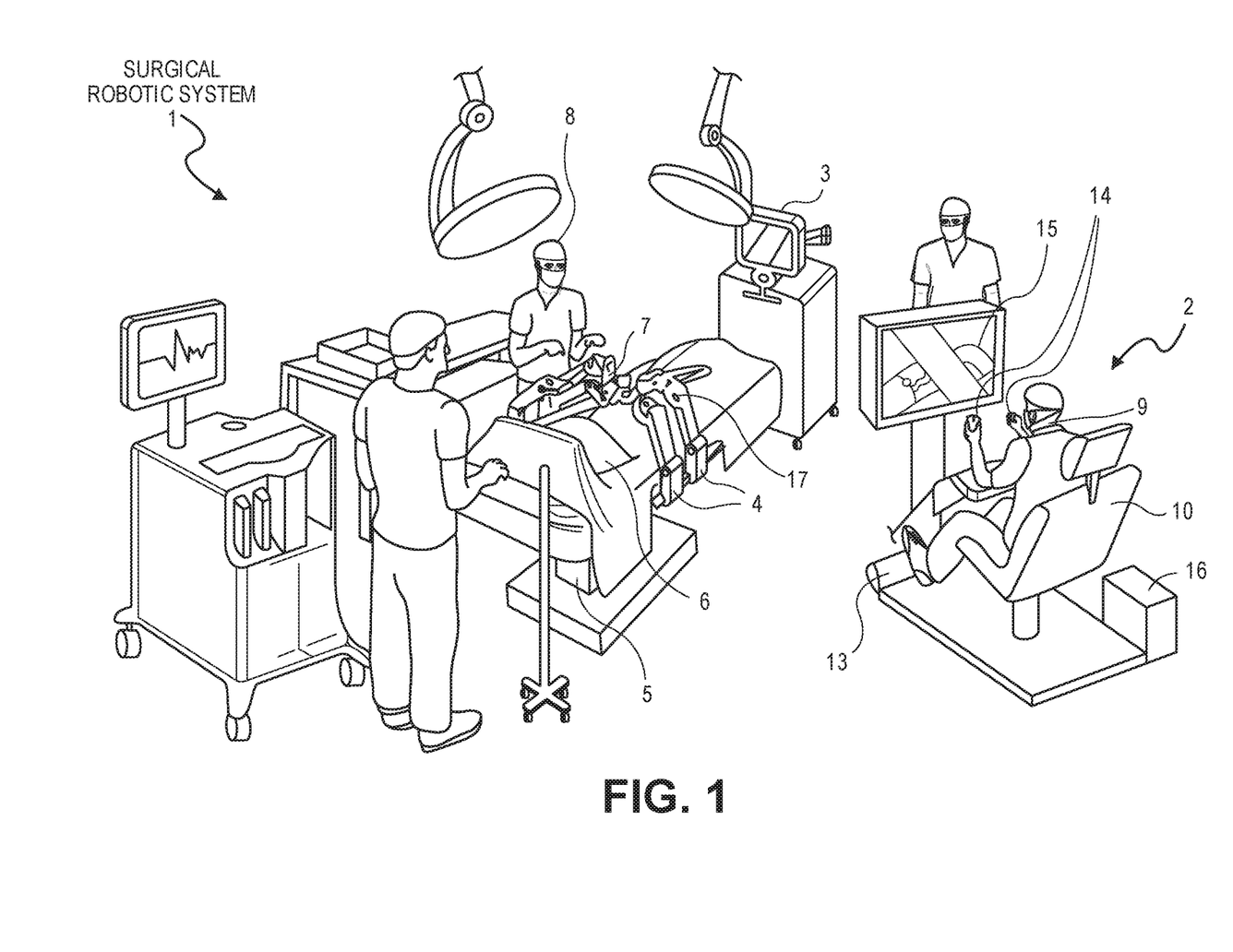
FIG. 1 is a pictorial view of an example surgical robotic system in an operating arena, in accordance with an embodiment.

Referring to FIG. 1, this is a pictorial view of an example surgical robotic system 1 in an operating arena. The system 1 includes a user console 2, a control tower 3, and one or more surgical robotic arms 4 at a surgical robotic platform 5, e.g., a table, a bed, etc. The arms 4 may be mounted to a table or bed on which the patient rests as shown in the example of FIG. 1, or they may be mounted to a cart separate from the table or bed. The system 1 can incorporate any number of devices, tools, or accessories used to perform surgery on a patient 6. For example, the system 1 may include one or more surgical tools 7 used to perform surgery. A surgical tool 7 may be an end effector that is attached to a distal end of a surgical arm 4, for executing a surgical procedure.

Each surgical tool 7 may be manipulated manually, robotically, or both, during the surgery. For example, the surgical tool 7 may be a tool used to enter, view, or manipulate an internal anatomy of the patient 6. In one aspect, the surgical tool 7 is a grasper that can grasp tissue of the patient. The surgical tool 7 may be configured to be controlled manually by a bedside operator 8, robotically via actuated movement of the surgical robotic arm 4 to which it is attached, or both. The robotic arms 4 are shown as being table-mounted but in other configurations the arms 4 may be mounted to a cart, the ceiling or a sidewall, or to another suitable structural support.

A remote operator 9, such as a surgeon or other human operator, may use the user console 2 to remotely manipulate the arms 4 and their attached surgical tools 7, e.g., referred to here as teleoperation. The user console 2 may be located in the same operating room as the rest of the system 1 as shown in FIG. 1. In other environments however, the user console 2 may be located in an adjacent or nearby room, or it may be at a remote location, e.g., in a different building, city, or country. The user console 2 may comprise a seat 10, foot-operated controls 13, one or more handheld user input devices (UIDs) 14, and at least one user display 15 that is configured to display, for example, a view of the surgical site inside the patient 6. In the example user console 2, the remote operator 9 is sitting in the seat 10 and viewing the user display 15 while manipulating a foot-operated control 13 and a handheld UID 14 in order to remotely control the arms 4 and the surgical tools 7 that are mounted on the distal ends of the arms 4.

In some variations, the bedside operator 8 may operate the system 1 in an "over the bed" mode in which the beside operator 8 (user) is at a side of the patient 6 and is simultaneously manipulating a robotically-driven tool (an end effector that is attached to the arm 4) with a handheld UID 14 held in one hand, and a manual laparoscopic tool in another hand. For example, the bedside operator's left hand may be manipulating the handheld UID to control a robotically-driven tool, while the bedside operator's right hand may be manipulating a manual laparoscopic tool. In this particular variation of the system 1, the bedside operator 8 can perform both robotic-assisted minimally invasive surgery and manual laparoscopic surgery on the patient 6.

During an example procedure (surgery), the patient 6 is prepped and draped in a sterile fashion to achieve anesthesia. Initial access to the surgical site may be performed manually while the arms of the robotic system 1 are in a stowed configuration or withdrawn configuration (to facilitate access to the surgical site.) Once access is completed, initial positioning or preparation of the robotic system 1 including its arms 4 may be performed. Next, the surgery proceeds with the remote operator 9 at the user console 2 utilizing the foot-operated controls 13 and the UIDs 14 to manipulate the various end effectors and perhaps an imaging system, to perform the surgery. Manual assistance may also be provided at the procedure bed or table, by sterile-gowned bedside personnel, e.g., the bedside operator 8 who may perform tasks such as retracting tissues, performing manual repositioning, and tool exchange upon one or more of the robotic arms 4. Non-sterile personnel may also be present to assist the remote operator 9 at the user console 2. When the procedure or surgery is completed, the system 1 and the user console 2 may be configured or set in a state to facilitate post-operative procedures such as cleaning or sterilization and healthcare record entry or printout via the user console 2.

In one embodiment, the remote operator 9 holds and moves the UID 14 to provide an input command to move a robot arm actuator 17 in the robotic system 1. The UID 14 may be communicatively coupled to the rest of the robotic system 1, e.g., via a console computer system 16. The UID 14 can generate spatial state signals corresponding to movement of the UID 14, e.g. position and orientation of the handheld housing of the UID, and the spatial state signals may be input signals to control a motion of the robot arm actuator 17. The robotic system 1 may use control signals derived from the spatial state signals, to control proportional motion of the actuator 17. In one embodiment, a console processor of the console computer system 16 receives the spatial state signals and generates the corresponding control signals. Based on these control signals, which control how the actuator 17 is energized to move a segment or link of the arm 4, the movement of a corresponding surgical tool that is attached to the arm may mimic the movement of the UID 14. Similarly, interaction between the remote operator 9 and the UID 14 can generate for example a grip control signal that causes a jaw of a grasper of the surgical tool 7 to close and grip the tissue of patient 6.

The surgical robotic system 1 may include several UIDs 14, where respective control signals are generated for each UID that control the actuators and the surgical tool (end effector) of a respective arm 4. For example, the remote operator 9 may move a first UID 14 to control the motion of an actuator 17 that is in a left robotic arm, where the actuator responds by moving linkages, gears, etc., in that arm 4. Similarly, movement of a second UID 14 by the remote operator 9 controls the motion of another actuator 17, which in turn moves other linkages, gears, etc., of the robotic system 1. The robotic system 1 may include a right arm 4 that is secured to the bed or table to the right side of the patient, and a left arm 4 that is at the left side of the patient. An actuator 17 may include one or more motors that are controlled so that they drive the rotation of a joint of the arm 4, to for example change, relative to the patient, an orientation of an endoscope or a grasper of the surgical tool 7 that is attached to that arm. Motion of several actuators 17 in the same arm 4 can be controlled by the spatial state signals generated from a particular UID 14. The UIDs 14 can also control motion of respective surgical tool graspers. For example, each UID 14 can generate a respective grip signal to control motion of an actuator, e.g., a linear actuator, which opens or closes jaws of the grasper at a distal end of surgical tool 7 to grip tissue within patient 6.

In some aspects, the communication between the platform 5 and the user console 2 may be through a control tower 3, which may translate user commands that are received from the user console 2 (and more particularly from the console computer system 16) into robotic control commands that transmitted to the arms 4 on the robotic platform 5. The control tower 3 may also transmit status and feedback from the platform 5 back to the user console 2. The communication connections between the robotic platform 5, the user console 2, and the control tower 3 may be via wired and/or wireless links, using any suitable ones of a variety of data communication protocols. Any wired connections may be optionally built into the floor and/or walls or ceiling of the operating room. The robotic system 1 may provide video output to one or more displays, including displays within the operating room as well as remote displays that are accessible via the Internet or other networks. The video output (video feed) may also be encrypted to ensure privacy and all or portions of the video output may be saved to a server or electronic healthcare record system.

It will be appreciated that the operating room scene in FIG. 1 is illustrative and may not accurately represent certain medical practices.

Figure 2:
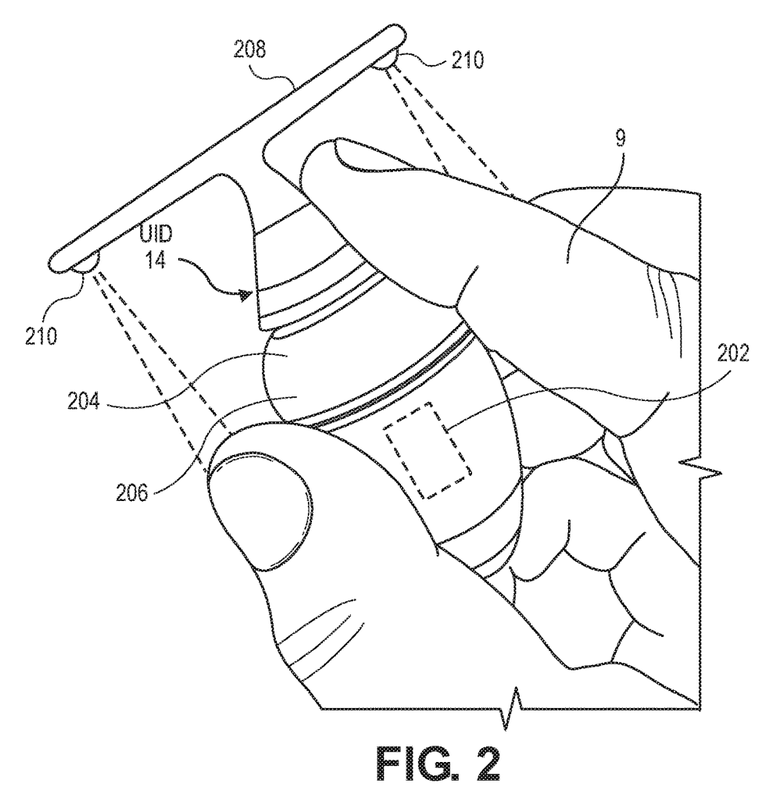
FIG. 2 is a pictorial view of a user interface device being held by a user, in accordance with an embodiment.

Referring to FIG. 2, a pictorial view of a user interface device being held by a user is shown in accordance with an embodiment. As described above, a user, e.g., the remote operator 9, can hold and move the UID 14 to control spatial motion of a corresponding surgical tool 7 of the surgical robotic system 1. The UID 14 can include a tracking sensor 202, e.g., a six-degree-of-freedom electromagnetic tracker, that is used for generating a spatial state signal, e.g., an input pose signal, in response to movement of a device body 206. More particularly, the tracking sensor 202 may be any sensor configured to track movement of the UID 14 in six degrees of freedom. The spatial state signal can be used by one or more processors to control a spatial motion of the arm actuator 17 and/or the surgical tool 7 of the surgical robotic system 1. Accordingly, the UID 14 can be used to control highly dexterous, precise movement of the robotic actuator 17 and/or the robotic surgical tool 7. Furthermore, in addition to detecting an orientation of the UID 14, tracking data from the tracking sensor 202 may be used to determine a location, speed, or acceleration of the UID 14.

The UID 14 can include a device housing 204 that is gripped by the user to manipulate the UID 14 and generate the spatial state signals. For example, the device housing 204 can include the device body 206 that has a shape that is easily gripped and manipulated by the user. The tracking sensor 202 can be mounted on or contained within the device body 206. For example, the tracking sensor 202 may be surrounded by an outer surface of the device body 206 and located at or near a center of gravity of the UID 14.

The device housing 204 may also include a device head 208. The device head 208 can extend distally from the device body 206. The device head 208 can have a surface extending transverse to a central axis of the device body 206. The device head 208 can be distal to the device body 206, and the transverse surface may be axially aligned with the user's hand when the user 9 is gripping the device body 206. In an embodiment, the UID 14 includes one or more proximity sensors 210. For example, several proximity sensors 210 can be mounted on the device housing 204 and directed toward the user's hand when the user 9 is gripping the device body 206. As shown in FIG. 2, the proximity sensors 210 may be mounted on the transverse surface of the device head 208 and the sensing path of the sensors can be directed proximally in a direction of the central axis of the UID 14 to detect the fingers of the user during surgery. For example, the UID 14 can include three or more, e.g., six, proximity sensors 210 evenly distributed around the central axis of the device body 206 on the device head 208. The proximity sensors 210 may be distributed such that the sensor group is able to detect the presence of the fingers at any location around the device body 206. More particularly, the proximity sensors 210 can detect a target within an annular target zone extending around the device body 206. Accordingly, in addition to receiving tracking data from the tracking sensor 202 indicative of a location or movement of the UID 14, the surgical robotic system 1 can receive proximity measures from the proximity sensors 210 indicative of whether the UID 14 is being held by the user 9, or indicative of whether an object is adjacent to or near the proximity sensors 210.

The proximity sensor(s) 210 can include sensors that detect the presence of nearby objects without physically contacting the objects. A variety of proximity sensor types exist that may be incorporated into the UID 14 for such purpose. For example, the proximity sensor(s) 210 can be capacitive proximity sensors, photoelectric sensors, or other types of proximity sensors. In an embodiment, the proximity sensor(s) 210 include time-of-flight (TOF) sensor(s) mounted on the device housing 204. The time-of-flight sensors can be used for range imaging. For example, the TOF sensors can emit a beam of electromagnetic radiation, e.g., an infrared laser beam emitted by an infrared laser source of the sensor, and measure a return signal reflected by a nearby object to determine a presence of or a distance to the nearby object. Accordingly, the proximity measures indicative of whether an object is adjacent to or near the proximity sensors 210 can be TOF measures output by TOF sensors indicative of a distance from the TOF sensors to the fingers of the user 9 or to another nearby object, such as a dock of the user console 2.

The proximity measures from the proximity sensor(s) 210 may be used to provide drop detection for the surgical robotic system 1. Proximity measures from the proximity sensor(s) 210 can indicate the presence of the user's hand when the user is holding the UID 14, and by contrast, can indicate the absence of the user's hand when the user is not holding the UID 14. Accordingly, the proximity measures can indicate a change from the presence of the user's hand to the absence of the user's hand when the user drops the UID 14. In an embodiment, the surgical robotic system 1 can halt motion of the surgical tool 7 in response to detecting the drop condition based on the proximity measures. Such drop detection and control of the surgical tool 7 can provide a safety feature to avoid unintended movements of the surgical tool 7 that could harm the patient 6.

Figure 3:
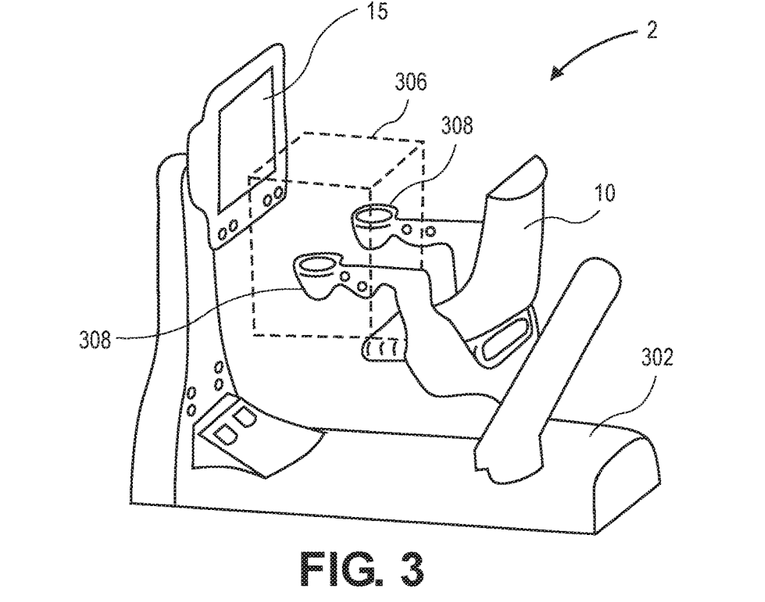
FIG. 3 is a perspective view of a user console of a surgical robotic system having a dock to hold a user interface device, in accordance with an embodiment.

Referring to FIG. 3, a perspective view of a user console of a surgical robotic system having a dock to hold a user interface device is shown in accordance with an embodiment. The user console 2 can include a base 302 to support the seat 10 and the display 15 of the surgical robotic system 1. The remote operator 9 may sit on the seat 10 and hold the UID 14 to control the surgical tool 7 being viewed on the display 15 during a surgical procedure.

The user console 2 can include a tracking subsystem to monitor movement of the UID 14. For example, the tracking subsystem can be an optical tracking subsystem including components to monitor movement of the UID 14 based on detection of a marker on the UID 14. The marker may be identifiable in an image to determine a position or orientation of the UID 14. The tracking subsystem may be an electromagnetic (EM) tracking subsystem having an EM source. The EM source can generate an EM tracking space 306, and the remote operator 9 can hold the UID 14 within the EM tracking space 306 to cause movement of the surgical tool 7 during the surgical procedure. More particularly, the EM tracking space 306 may be the workspace within which the remote operator 9 may move the UID 14 to generate the spatial state signals.

The user console 2 may include a source of an EM field (not shown), such as an EM generator having a field generator to generate a position varying magnetic field that is used to establish a coordinate space. Accordingly, the EM generator can generate the EM field of the workspace within which the UID 14 is manipulated. The EM field can be the EM tracking space 306. In an embodiment, the tracking sensor 202 can be a magnetic tracking probe capable of measuring six degrees of freedom within the EM tracking space 306. The tracking sensor 202 can be a sensor containing coils in which current is induced via the EM field. The tracking sensor 202 can have a known response to the EM field, and the response may be measured. By measuring the coil behavior, a position and orientation of the tracking sensor 202, and thus the UID 14, can be determined. The measured response may be output as the spatial state signal (UID EM readings) representing movement of the UID 14 within the EM tracking space 306. Furthermore, tracking data from the tracking sensor 202 can be used to determine a location or motion of the UID 14 within the tracking space 306.

In an embodiment, the user console 2 includes one or more docks 308. A dock 308 can include a structure, such as a receptacle, to receive the UID 14. The dock 308 can hold the UID 14 at the beginning of a surgical procedure. Similarly, the UID 14 can be intermittently placed in the dock 308 throughout the surgical procedure to allow the surgeon to rest or attend to other objects. The dock 308 can be placed within the EM tracking space 306 of the user console 2. While the UID 14 is positioned within the dock 308, tracking data from the tracking sensor 202 can indicate that the UID 14 is positioned in the dock 308 and/or whether the UID 14 is moving.

As described above, the proximity sensor(s) 210 provide proximity measures that can be used in a drop detection algorithm to determine whether the user is holding the UID 14. Proper function and accuracy of the proximity sensor(s) 210 can therefore facilitate safe function of the surgical robotic system 1. Accordingly, verifying the function and accuracy of the proximity sensors can help assure patient safety. In an embodiment, the surgical robotic system 1 can verify the functionality of the UID 14 and the accuracy of the proximity sensor(s) 210 through self-testing of the UID 14 when the UID 14 is placed in the dock 308 before or during the surgical procedure.

Figure 4:
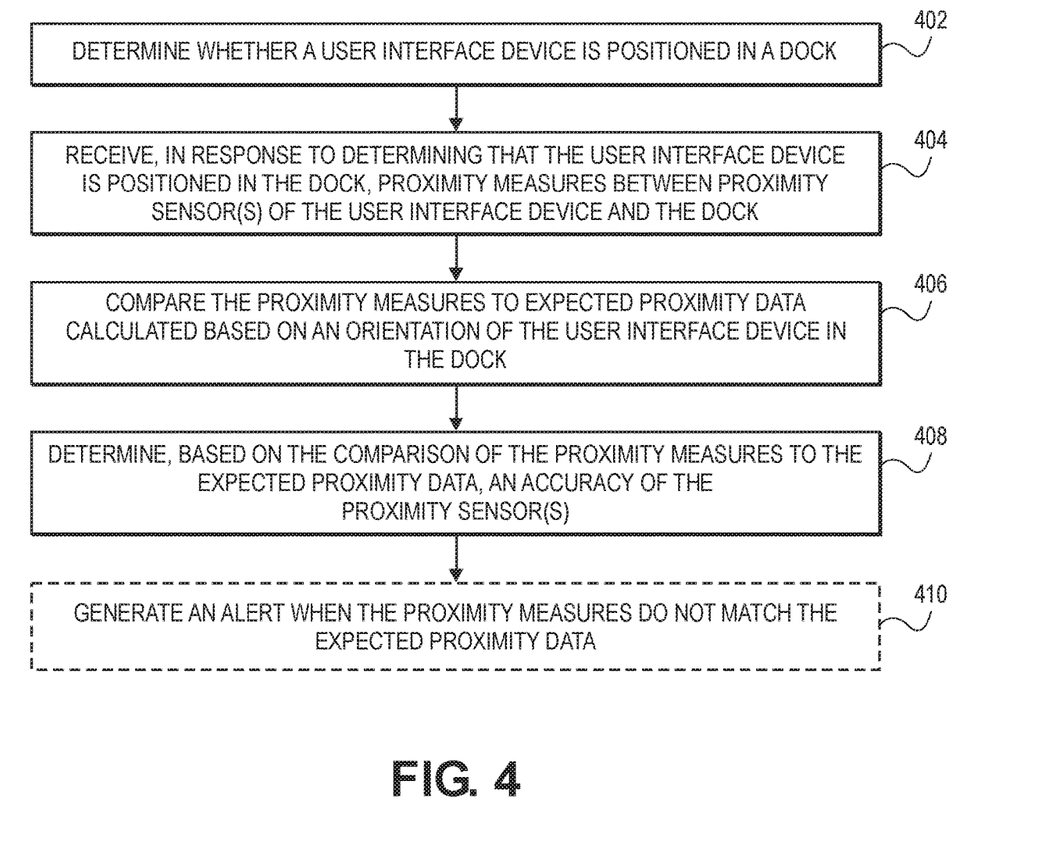
FIG. 4 is a flowchart of a method of verifying functionality of a user interface device of a surgical robotic system, in accordance with an embodiment.

Referring to FIG. 4, a flowchart of a method of verifying functionality of a user interface device of a surgical robotic system is shown in accordance with an embodiment. Self-testing of the UID 14 can be performed when the UID 14 is placed in a known physical constraint, such as the dock 308. The method of verifying UID 14 functionality through the self-test includes several operations, which are referred to below in combination with FIGS. 5-8.

Figure 5:
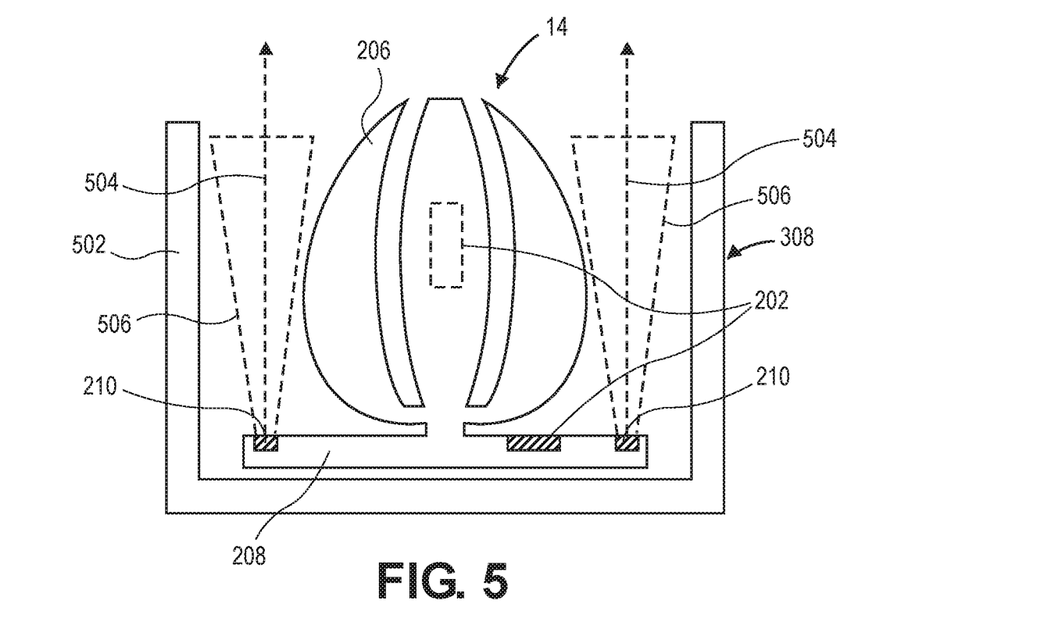
FIG. 5 is a side view of a user interface device positioned within a dock in a first orientation, in accordance with an embodiment.

Referring to FIG. 5, a side view of a user interface device positioned within a dock in a first orientation is shown in accordance with an embodiment. The self-test may be performed during startup of the surgical robotic system 1. The UID 14 is usually in the dock 308 at startup, and thus, the beginning of the surgical procedure provides an opportunity to perform the method described below. It will be appreciated, however, that the check may be done intraoperatively any time the user places the UID 14 in the dock 308. For example, the self-test may be triggered each time the UID 14 is docked. Accordingly, at operation 402, the self-test can be triggered when the surgical robotic system 1 determines whether the UID 14 is positioned in the dock 308.

Determining whether the UID 14 is positioned in the dock 308 may include determining a location and/or a motion of the UID 14. More particularly, the determination can depend upon data indicating that the UID 14 is positioned in the dock 308 or data indicating that the UID 14 is stationary. The location and/or motion data may be received from tracking sensor 202. For example, tracking data from an IMU or an EM sensor contained within the UID 14 can be used to determine whether the UID 14 is positioned in or near the dock 308. Tracking data indicating that the UID 14 is near the dock 308 may exist even when the user is manipulating the UID 14 in the vicinity of the dock 308. Accordingly, tracking data from the IMU or the EM sensor may further be used to determine whether the UID 14 is stationary. More particularly, the system can determine that the UID 14 is positioned in the dock 308 based on the UID 14 being located near the dock 308 and the UID 14 being stationary.

At operation 404, when the UID 14 is determined to be positioned in the dock 308, the system may responsively receive proximity measures from the one or more proximity sensors 210 to initiate the self-test of the UID 14. The proximity measures can be between the proximity sensor(s) 210 of the UID 14 and the dock 308. As described above, the proximity measures received from the proximity sensor(s) 210 can indicate a presence or an absence of adjacent structures. For example, the dock 308 may have a sidewall 502 forming a receptacle to receive the UID 14, and depending upon an orientation of the UID 14 within the dock 308, the proximity sensor(s) 210 may or may not detect the sidewall 502. For example, when the UID 14 is properly seated in the dock 308, a line of sight 504 of the proximity sensor(s) 210 may be parallel to the sidewall 502. Accordingly, when the UID 14 is properly seated in the dock 308, TOF sensors may be expected to receive no reflected signal from the light cones 506 emitted upward through the dock cavity.

Figure 6:
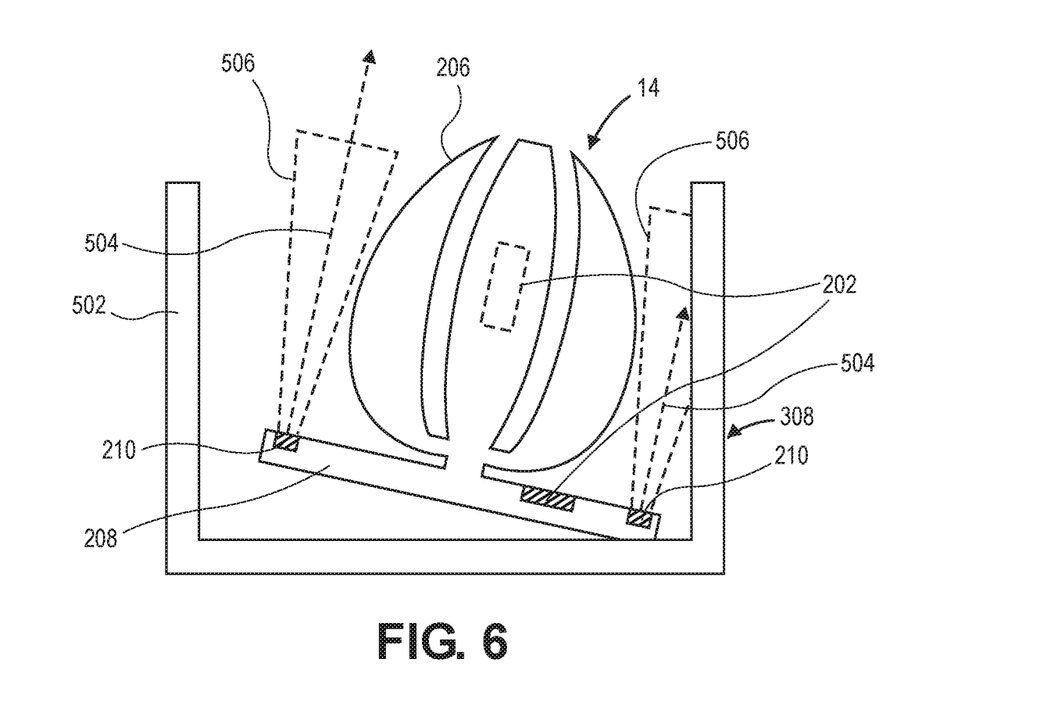
FIG. 6 is a side view of a user interface device positioned within a dock in a second orientation, in accordance with an embodiment.

Referring to FIG. 6, a side view of a user interface device positioned within a dock in a second orientation is shown in accordance with an embodiment. The user may inadvertently place the UID 14 imperfectly in the dock 308. In such case, the light cones 506 emitted by one or more of the proximity sensors 210 may be occluded by the sidewall 502. For example, the UID 14 may be tilted within the dock cavity such that the central axis of the device body 206 is misaligned with a central axis of the dock 308. As a result of the misalignment, the line of sight 504 of one or more proximity sensors 210 can intersect the sidewall 502. Thus, the emitted light can reflect back and downward to the proximity sensor 210, indicating the presence of the sidewall 502. By contrast, a light cone 506 of another proximity sensor 210 can be emitted outward and upward from the dock cavity.

Each orientation of the UID 14 in the dock 308 can correspond to a respective set of sensor data. For example, a signature of the orientation shown in FIG. 5, in which the UID 14 is properly seated in the dock 308, can include sensor values for each proximity sensor that are minimum range values. The minimum range values can correspond to no or minimal reflections of the light cones 506 that are emitted through the dock cavity. By contrast, a signature of the orientation shown in FIG. 6, in which the UID 14 is tilted within the dock 308, can include sensor values for one or more proximity sensors that are greater than the minimum range values. The higher range values can indicate reflections from the sidewall 502 from the proximity sensors having a line of sight 504 intersecting the dock 308. Furthermore, one or more of the proximity sensors can have the minimum range values, corresponding to proximity sensors having a line of sight 504 that does not intersect the dock 308. Accordingly, the proximity measures, such as TOF readings from TOF sensors, can depend on and correspond to a geometry of the dock 308 and the orientation of the UID 14 within the dock 308.

At operation 406, the proximity measures received from the proximity sensor(s) 210 can be compared to expected proximity data (e.g., TOF data). In an embodiment, the expected proximity data is the proximity data corresponding to the geometry of the dock 308 and respective orientations of the UID 14 within the dock 308. The expected proximity data can be collected through previous calibration operations, e.g., measurements made of UIDs 14 in different orientations. The expected proximity data can be calculated based on an orientation of the UID 14 in the dock 308. For example, the expected proximity data can be collected via calculations, e.g., via numerical models that simulate the expected output of every proximity sensor 210 for various UID orientations when the UID 14 is in the dock. Accordingly, the expected proximity data corresponds to respective orientations of the UID 14 in the dock 308. For example, the expected proximity data can have the signature of the proximity measures for the UID 14 properly seated within the dock 308 (FIG. 5) or tilted within the dock 308 (FIG. 6). Of course, the expected proximity data can correspond to a multitude of orientations, and for each orientation, the expected proximity data can include a particular set of range values for the sensors when the UID 14 is so oriented. The expected proximity data can be stored in a memory of the user console 2 for retrieval when needed.

In an embodiment, the proximity measures received from the UID 14 is compared to expected proximity data for a presumed orientation of the device. For example, it may be presumed that the surgeon will properly place UID 14 in the dock 308, as shown in FIG. 5. This presumption may be strengthened when the dock 308 is designed to receive the UID 14 in only a single orientation. For example, an opening to receive the device head 208 may have a same size and profile as the device head 208 such that the UID 14 can only be inserted into the dock 308 in one orientation. In such case, the proximity measures received from the UID 14 may be compared to the expected proximity data corresponding to the orientation of the UID 14 when the UID 14 is properly seated in the dock 308.

It may not be possible to ensure that the UID 14 is perfectly aligned in the dock 308 each time the user returns the UID 14. As described above, the user may inadvertently place the UID 14 in the dock 308 such that the device is tilted as shown in FIG. 6, or otherwise askew within the dock 308. In an embodiment, rather than compare the proximity measures to expected proximity data based on a presumed orientation, the proximity measures received from the UID 14 is compared to expected proximity data based on a known orientation of the device. The orientation of the UID 14 may be determined based on tracking data from the tracking sensor 202, e.g., an IMU or EM sensor (or other tracking technology). The user console 2 can receive, in response to determining that the UID 14 is positioned in the dock 308, tracking data from the tracking sensor 202. The tracking data can be used to determine the orientation, e.g., a tilt, of the UID 14. Based on the tracking data, the user console 2 can determine the expected proximity data. More particularly, the tracking sensor 202 readings can be mapped to expected proximity data for the tracked orientation. By way of example, when the tracking data indicates that the UID 14 has the orientation shown in FIG. 5, expected proximity data having the signature minimal range values may be retrieved from memory. Similarly, when the tracking data indicates that the UID 14 has the orientation shown in FIG. 6, expected proximity data having the signature minimal and higher range values may be retrieved from memory. Accordingly, the orientation determined from the tracking data can be mapped to an expected set of proximity sensor readings that depends on the geometry of the dock 308 and the orientation of the UID 14 within the dock 308.

At operation 408, the system can determine, based on the comparison of the proximity measures to the expected proximity data, an accuracy of the proximity sensor(s) 210. A match between the proximity measures, received from the proximity sensor(s) 210 when the UID 14 is in a given orientation, and the expected proximity data, corresponding to accurate proximity sensor(s) 210 in the given orientation, indicates that the proximity sensor(s) 210 are functioning properly. Accordingly, the proximity sensor(s) 210 are determined to be accurate when the proximity measures match the expected proximity data. By contrast, when the proximity measures do not match expected proximity data, it may be determined that the proximity sensor(s) 210 are not working.

As used herein, a match between the proximity measures and the expected proximity data may not require a proximity data value for every proximity sensor 210 to equal a corresponding expected proximity data value of the modeled expectation. Rather, the proximity data values may be within a same range, or within a percent difference, of the corresponding expected proximity data value. For example, the proximity data may match the expected proximity data when each proximity data value is within a predetermined percentage, e.g., 20%, of a corresponding expected proximity data value.

Depending on whether the output of proximity sensor(s) 210 match the expectation, it can be determined whether proximity sensor(s) 210 of the UID 14 are operating correctly. Such verification of the UID 14 functionality can increase confidence in the accuracy of the proximity sensor(s) 210 in at least one orientation. By continually checking the proximity sensor(s) 210 each time the user places the UID 14 in the dock 308, the confidence that the sensor readings are correct can be further increased. Accordingly, the self-test to verify UID 14 functionality can be performed multiple times throughout the surgical procedure, and each time the test passes, the confidence in the accuracy of the proximity sensor(s) 210 can improve. When the self-test passes, the user may continue to use the UID 14 with confidence that drop detection is enable and the system is functioning safely.

In the event that the proximity measures does not match the expected proximity data, at operation 410, the system may generate an alert to notify the user that the UID 14 functionality is currently compromised. In an embodiment, the alert can notify the user and request that the user remove and replace the UID 14 in the dock 308 to trigger a re-test of the UID 14 functionality. The alert may also guide the user through a recalibration of the proximity sensor(s) 210. Alternatively, the alert may notify the user and request that the user wait until the system has automatically recalibrated the proximity sensor(s) 210. In any case, the system can warn the user and/or disable control of the surgical tool 7 by the UID 14 until the issue is repaired and proper function of the UID 14 is verified.

The method of verifying functionality of the UID 14, as described above, can include a dock 308 having a known structure, e.g., predetermined geometry, obstacles, etc. The dock 308 as shown in FIGS. 5-6 may be referred to as a free support dock, which allows the UID 14 to be placed into the dock 308 receptacle in a variety of orientations. By contrast, the dock 308 may be a type of dock referred to as a fixture dock that constrains the orientation of the UID 14 when the UID 14 is positioned in the dock 308. An example of a fixture dock is described above with respect to the receptacle having an opening sized and configured to receive the UID 14 in only one orientation. As described below, however, another example of a fixture dock 308 can include a movable portion that constrains the orientation of the UID 14. As described, the fixture dock can also provide a movable reference surface to evaluate the accuracy of the proximity sensor(s) 210.

Figure 7:
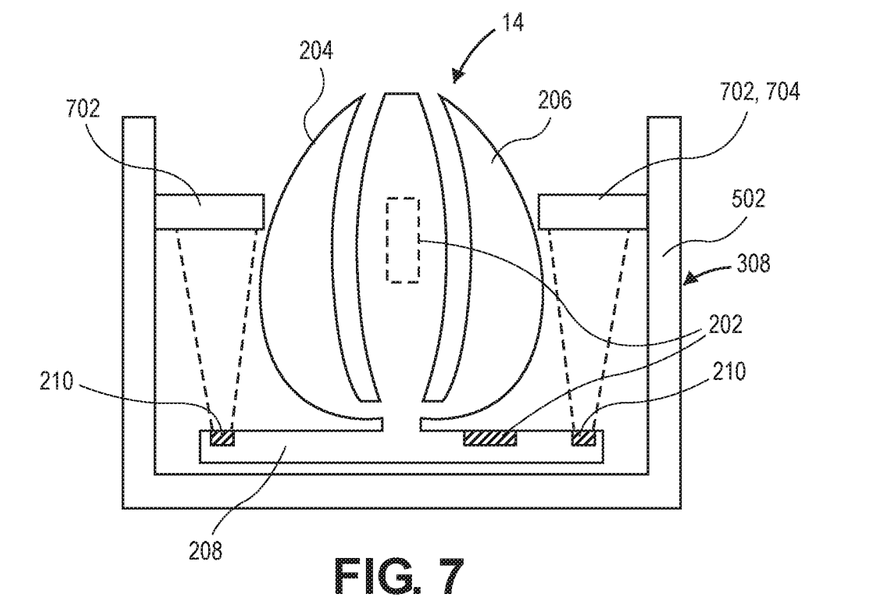
FIG. 7 is a side view of a user interface device positioned within a dock having a movable portion in a first state, in accordance with an embodiment.

Referring to FIG. 7, a side view of a user interface device positioned within a dock having a movable portion in a first state is shown in accordance with an embodiment. The dock 308 can include one or more movable portions 702 that can move between a first state and a second state. For example, the movable portion 702 may include a retractable prong 704 that can extend from, and be retracted into, the sidewall 502 of the dock 308. In the first state, the retractable prong 704 may be extended. By contrast, in the second state, the retractable prong 704 may be retracted.

When the retractable guides are extended, the guides can close around the device housing 204 of the UID 14. Accordingly, the movable portion 702 can physically constrain the UID 14 in a predetermined orientation. For example, even if the user were to place the UID 14 into the dock 308 in the tilted configuration shown in FIG. 6, when the retractable prongs 704 extend into the first state, the prongs would tip the UID 14 to align the central axes of the UID 14 and the dock 308. More particularly, the movable portion 702 can ensure that the UID 14 is properly seated within the dock 308 in the first state.

Given that the fixture dock 308 ensures a particular orientation of the UID 14 in the first state, the orientation of the UID 14 in the first state may be presumed. Accordingly, the proximity measures received when the movable portion 702 is in the first state can be compared to expected proximity data for the UID 14 in the presumed orientation. Of course, rather than presuming the orientation of the UID 14, additional sensor readings, e.g., from the tracking sensor 202, may be used to select the expected proximity data to compare to the proximity sensor readings in the first state. In either case, a functionality check can be performed on the proximity sensor(s) 210 in the first state when the UID 14 is constrained by the movable portion 702.

Figure 8:
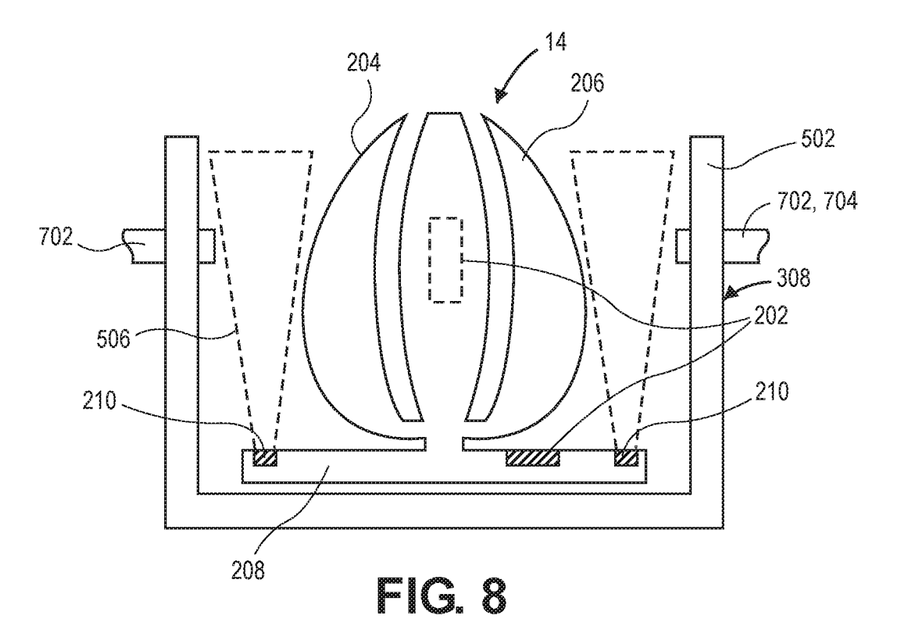
FIG. 8 is a side view of a user interface device positioned within a dock having a movable portion in a second state, in accordance with an embodiment.

Referring to FIG. 8, a side view of a user interface device positioned within a dock having a movable portion in a second state is shown in accordance with an embodiment. The retractable guides can allow for multiple self-tests to be performed while the UID 14 is positioned in the dock 308 in a single orientation. In an embodiment, the movable portion 702 can retract into the second state. The UID 14 can remain in the upright configuration even after the prongs retract because the device head 208 can provide a stable base for the device body 206. Although the orientation of the UID 14 remains the same, the received proximity measures may differ between the first state and the second state. The movable portion 702 can provide a reference surface that reflects sensor emissions in the first state, however, when the movable portion 702 is retracted it may avoid the light cones 506 of the sensors and therefore may not reflect the light back to the sensors.

The collection and analysis of additional proximity measures in several states of the dock 308 can provide additional data for mapping that may increase confidence in the detected accuracy of the proximity sensor(s) 210. The method of verifying functionality of the UID 14 may therefore include a secondary set of operations that repeat operations 404-408, described above, in the second state. More particularly, similar to operation 404, second proximity measures (e.g., second TOF measures) can be received from the proximity sensor(s) 210 when the movable portion 702 of the dock 308 is in the second state (e.g., when the alignment features are retracted). Similar to operation 406, the second proximity measures can be compared to second expected proximity data. The second expected proximity data may correspond to the orientation of the UID 14 in the dock 308 when the movable portion 702 is in the second state. For example, whereas the expected proximity data for the first state shown in FIG. 7 may represent maximum reflection from the extended prongs, the second expected proximity data for the second state shown in FIG. 8 may represent minimal reflection from the retracted prongs. Similar to operation 408, the second proximity measures can be compared to the second expected proximity data to determine the accuracy of the proximity sensor(s) 210. For example, when the actual proximity data matches the expected proximity data for the particular configuration of the dock 308 and the UID 14 in the second state, the system can verify that the proximity sensor(s) 210 are performing accurately and/or the UID 14 is functional and safe to use. If the second proximity measures do not match the second expected proximity data, the system can optionally generate the alert to notify the user, similar to operation 410. The system and/or the user may then take corrective action to recalibrate the UID 14 before continuing the surgical procedure.

Figure 9:
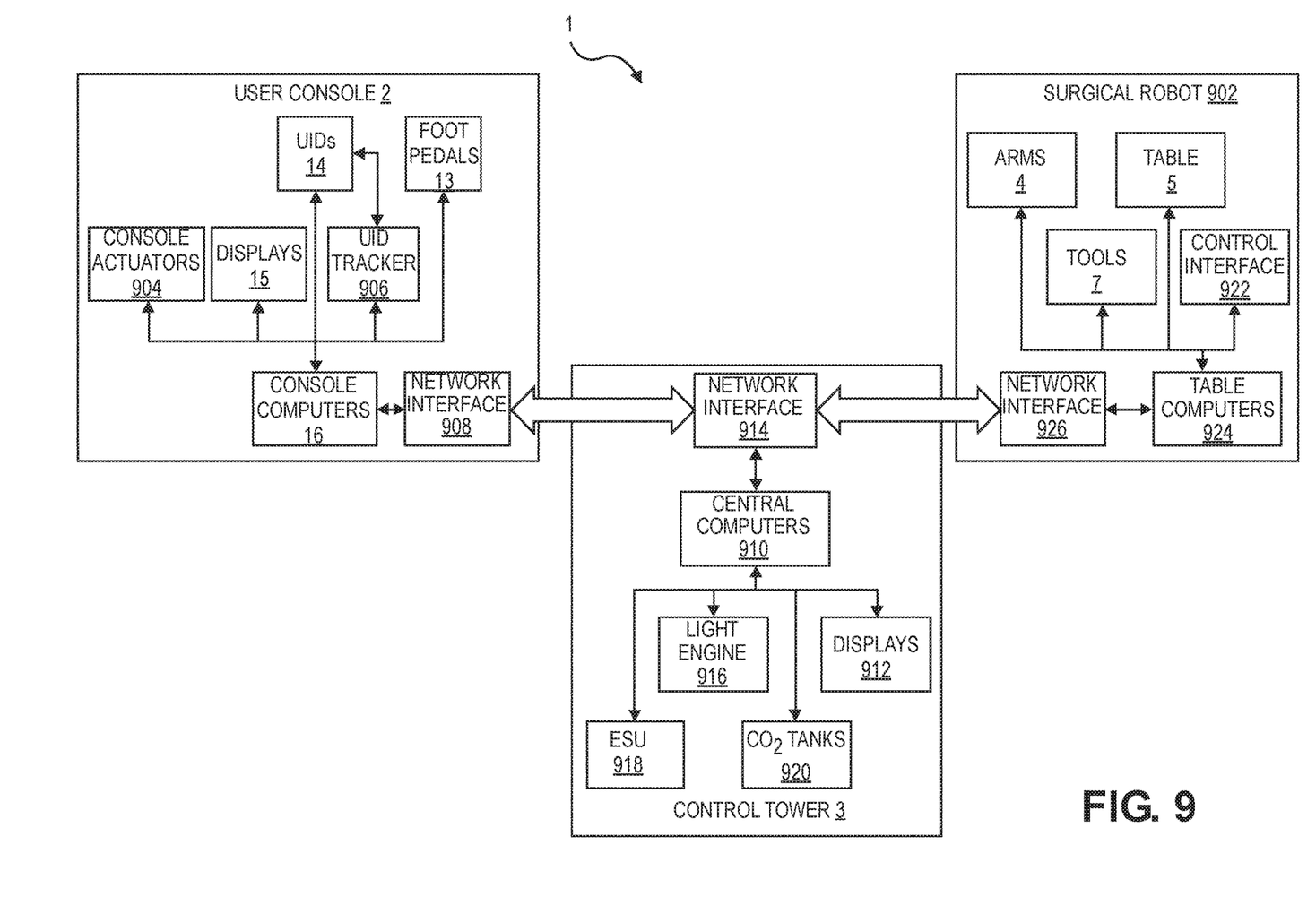
FIG. 9 is a block diagram of exemplary hardware components of a surgical robotic system, in accordance with an embodiment.

Referring to FIG. 9, a block diagram of exemplary hardware components of a surgical robotic system is shown in accordance with an embodiment. The exemplary surgical robotic system 1 may include the user console 2, a surgical robot 902, and the control tower 3. The hardware components of the surgical robotic system 1 can include one or more processors configured to perform the methods described above. More particularly, the one or more processors, e.g., of the user console 2, may execute instructions stored on a non-transitory computer-readable medium to cause the surgical robotic system 1 to perform the methods described above. Furthermore, the surgical robotic system 1 may include other additional hardware components; thus, the diagram is provided by way of example and not limitation to the system architecture.

As described above, the user console 2 comprises console computer systems 16 and one or more UIDs 14. User console 2 can include console actuators 904, displays 15, a UID tracker 906, foot pedals 13, and a network interface 908. A user or surgeon sitting at the user console 2 can perform robot-assisted surgeries by controlling the surgical robot 902 using the one or more UIDs 14 and foot pedals 13. Positions and orientations of the UIDs 14 are continuously tracked by the UID tracker 906, and status changes are recorded by the console computers 16 as user input and dispatched to the control tower 3 via the network interface 1008. The tracking data from the UID tracker 906 and the proximity data from the UIDs 14 can be used by one or more processors of the console computers 16 to perform drop detection or UID self-testing, as described above. Real-time surgical video of patient anatomy, instrumentation, and relevant software apps can be presented to the user on the high resolution 3-D displays 15 including open or immersive displays.

Unlike other existing surgical robotic systems, the user console 2 disclosed herein may be communicatively coupled to the control tower 3 over a single fiber optic cable. The control tower 3 can be a mobile point-of-care cart housing touchscreen displays, computers that control the surgeon's robotically-assisted manipulation of instruments, safety systems, graphical user interface (GUI), light source, and video and graphics computers. As shown in FIG. 9, the control tower 3 may comprise central computers 910 including at least a visualization computer, a control computer, and an auxiliary computer, various displays 912 including a team display and a nurse display, and a network interface 914 coupling the control tower 3 to both the user console 2 and the surgical robot 902. The control tower 3 may also house third-party devices, such as an advanced light engine 916, an electrosurgical generator unit (ESU) 918, and insufflator and $CO_2$ tanks 920. The control tower 3 may offer additional features for user convenience, such as the nurse display touchscreen, soft power and E-hold buttons, user-facing USB for video and still images, and electronic caster control interface. The auxiliary computer may also run a real-time Linux, providing logging/monitoring and interacting with cloud-based web services.

The surgical robot 902 comprises an articulated operating table 5 with a plurality of integrated arms 4 that can be positioned over the target patient anatomy. A suite of compatible tools 7 can be attached to or detached from the distal ends of the arms 4, enabling the surgeon to perform various surgical procedures. The surgical robot 902 may also comprise control interface 922 for manual control of the arms 4, table 5, and tools 7. The control interface can include items such as, but not limited to, remote controls, buttons, panels, and touchscreens. Other accessories such as trocars (sleeves, seal cartridge, and obturators) and drapes may also be needed to perform procedures with the system. In some variations the plurality of arms 4 include forearms mounted on both sides of the operating table 5, with two arms on each side. For certain surgical procedures, an arm mounted on one side of the table can be positioned on the other side of the table by stretching out and crossing over under the table and arms mounted on the other side, resulting in a total of three arms positioned on the same side of the table 5. The surgical robot 902 can also comprise table computers 924 and a network interface 926, which can place the surgical robot 902 in communication with the control tower 3.

In the foregoing specification, the invention has been described with reference to specific exemplary embodiments thereof. It will be evident that various modifications may be made thereto without departing from the broader spirit and scope of the invention as set forth in the following claims. The specification and drawings are, accordingly, to be regarded in an illustrative sense rather than a restrictive sense.

What is claimed is:

1. A method of verifying functionality of a user interface device of a surgical robotic system, the method comprising:
    determining whether the user interface device is positioned in a dock of the surgical robotic system;
    receiving, in response to determining that the user interface device is positioned in the dock, proximity measures between one or more proximity sensors of the user interface device and the dock;

comparing the proximity measures to expected proximity data calculated based on an orientation of the user interface device in the dock; and determining, based on the comparison of the proximity measures to the expected proximity data, an accuracy of the one or more proximity sensors.

2. The method of claim 1, wherein the proximity measures include time-of-flight measures.

3. The method of claim 1, wherein the expected proximity data corresponds to the orientation of the user interface device when the user interface device is properly seated in the dock, and wherein the one or more proximity sensors are determined to be accurate when the proximity measures match the expected proximity data.

4. The method of claim 1 further comprising:
receiving tracking data from a tracking sensor of the user interface device, wherein the tracking sensor is configured to track movement of the user interface device in six degrees of freedom and to generate spatial state signals for manipulating a spatial motion of a corresponding surgical tool of the surgical robotic system; and determining, based on the tracking data, the expected proximity data.

5. The method of claim 1 further comprising determining whether the user interface device is stationary, wherein determining whether the user interface device is positioned in the dock is based on whether the user interface device is stationary.

6. The method of claim 1 further comprising generating an alert when the proximity measures do not match the expected proximity data.

7. The method of claim 1, wherein the dock includes a movable portion, wherein the proximity measures are received when the movable portion is in a first state, and further comprising:
receiving second proximity measures from the one or more proximity sensors when the movable portion is in a second state;
comparing the second proximity measures to second expected proximity data, wherein the second proximity measures correspond to the orientation of the user interface device in the dock when the movable portion is in the second state; and
determining, based on the comparison between the second proximity measures and the second expected proximity data, the accuracy of the one or more proximity sensors.

8. A surgical robotic system, comprising:
a dock;
a user interface device having one or more proximity sensors; and
one or more processors configured to:
determine whether the user interface device is positioned in the dock,
receive, in response to determining that the user interface device is positioned in the dock, proximity measures between one or more proximity sensors of the user interface device and the dock,
compare the proximity measures to expected proximity data calculated based on an orientation of the user interface device in the dock, and
determine, based on the comparison of the proximity measures to the expected proximity data, an accuracy of the one or more proximity sensors.

9. The surgical robotic system of claim 8, wherein the one or more proximity sensors include one or more time-of-flight sensors mounted on a device housing of the user interface device.

10. The surgical robotic system of claim 8, wherein the expected proximity data corresponds to the orientation of the user interface device when the user interface device is properly seated in the dock, and wherein the one or more proximity sensors are determined to be accurate when the proximity measures match the expected proximity data.

11. The surgical robotic system of claim 8 further comprising:
receiving tracking data from a tracking sensor of the user interface device, wherein the tracking sensor is configured to track movement of the user interface device in six degrees of freedom and to generate spatial state signals for manipulating a spatial motion of a corresponding surgical tool of the surgical robotic system; and
determining, based on the tracking data, the expected proximity data.

12. The surgical robotic system of claim 8 further comprising determining whether the user interface device is stationary, wherein determining whether the user interface device is positioned in the dock is based on whether the user interface device is stationary.

13. The surgical robotic system of claim 8 further comprising generating an alert when the proximity measures do not match the expected proximity data.

14. The surgical robotic system of claim 8, wherein the dock includes a movable portion, wherein the proximity measures are received when the movable portion is in a first state, and further comprising:
receiving second proximity measures from the one or more proximity sensors when the movable portion is in a second state;
comparing the second proximity measures to second expected proximity data, wherein the second proximity measures correspond to the orientation of the user interface device in the dock when the movable portion is in the second state; and
determining, based on the comparison between the second proximity measures and the second expected proximity data, the accuracy of the one or more proximity sensors.

15. The surgical robotic system of claim 14, wherein the movable portion includes a retractable prong, and wherein the retractable prong is extended in the first state and retracted in the second state.

16. A non-transitory computer-readable medium storing instructions, which when executed by one or more processors of a surgical robotic system, cause the surgical robotic system to perform a method comprising:
determining whether a user interface device is positioned in a dock;
receiving, in response to determining that the user interface device is positioned in the dock, time-of-flight measures between one or more time-of-flight sensors of the user interface device and the dock;
comparing the time-of-flight measures to expected time-of-flight data calculated based on an orientation of the user interface device in the dock; and
determining, based on the comparison of the time-of-flight measures to the expected time-of-flight data, an accuracy of the one or more time-of-flight sensors.

17. The non-transitory computer-readable medium of claim 16, wherein the expected time-of-flight data corresponds to the orientation of the user interface device when the user interface device is properly seated in the dock, and wherein the one or more time-of-flight sensors are determined to be accurate when the time-of-flight measures match the expected time-of-flight data.

18. The non-transitory computer-readable medium of claim 16, wherein the method further comprises:

receiving tracking data from a tracking sensor of the user interface device, wherein the tracking sensor is configured to track movement of the user interface device in six degrees of freedom and to generate spatial state signals for manipulating a spatial motion of a corresponding surgical tool of the surgical robotic system; and determining, based on the tracking data, the expected time-of-flight data.

19. The non-transitory computer-readable medium of claim 16, wherein the method further comprises determining whether the user interface device is stationary, wherein determining whether the user interface device is positioned in the dock is based on whether the user interface device is stationary.

20. The non-transitory computer-readable medium of claim 16, wherein the dock includes a movable portion, wherein the time-of-flight measures are received when the movable portion is in a first state, and wherein the method further comprises:

receiving second time-of-flight measures from the one or more time-of-flight sensors when the movable portion is in a second state;

comparing the second time-of-flight measures to second expected time-of-flight data, wherein the second time-of-flight measures correspond to the orientation of the user interface device in the dock when the movable portion is in the second state; and determining, based on the comparison between the second time-of-flight measures and the second expected time-of-flight data, the accuracy of the one or more time-of-flight sensors.

\* \* \* \* \*